United States Patent [19]

Schaefer

[11] Patent Number: 4,856,741
[45] Date of Patent: Aug. 15, 1989

[54] ADJUSTABLE PATIENT SUPPORT TABLE FOR AN X-RAY DIAGNOSTICS INSTALLATION

[75] Inventor: Willi Schaefer, Erlangen, Fed. Rep. of Germany

[73] Assignee: Siemens Aktiengesellschaft, Berlin and Munich, Fed. Rep. of Germany

[21] Appl. No.: 130,279

[22] Filed: Dec. 8, 1987

[30] Foreign Application Priority Data

Dec. 22, 1986 [DE] Fed. Rep. of Germany ... 8634352[U]

[51] Int. Cl.$^4$ ............................................. A61B 6/00
[52] U.S. Cl. .................................... 248/122; 248/285; 248/282; 108/20; 108/92; 5/60; 5/508
[58] Field of Search ............... 248/121, 122, 124, 125, 248/282, 283, 285, 287, 327; 5/60, 507, 508; 297/330; 108/20, 92; 269/322

[56] References Cited

U.S. PATENT DOCUMENTS

| | | | |
|---|---|---|---|
| 1,682,180 | 8/1928 | Merrill | 248/285 |
| 1,796,354 | 3/1931 | Ahlberg | 248/282 |
| 3,366,430 | 1/1968 | Diedrich | 248/285 |
| 3,389,702 | 6/1968 | Kennedy | 5/508 |
| 3,423,057 | 1/1969 | Iverson | 248/283 |
| 3,550,892 | 12/1970 | Propst | 248/125 |
| 3,971,538 | 7/1976 | Marvich | 248/122 |
| 4,113,218 | 9/1978 | Linder | 248/124 |
| 4,557,453 | 12/1985 | McCloskey | 248/283 |

FOREIGN PATENT DOCUMENTS

| | | | |
|---|---|---|---|
| 789207 | 7/1968 | Canada | 5/508 |
| 1406564 | 6/1965 | France | 248/282 |
| 2255038 | 7/1975 | France | . |
| 347604 | 8/1960 | Sweden | . |

Primary Examiner—Ramon O. Ramirez
Assistant Examiner—Robert A. Olson
Attorney, Agent, or Firm—Hill, Van Santen, Steadman & Simpson

[57] ABSTRACT

An x-ray diagnostics installation has an adjustable patient support table, with a control box for positioning the table, the control box also being adjustable relative to the table. The control box is attached to a bracket which is mounted in the region of the foot end of the patient support table, and is displaceable via the bracket in a direction parallel to a longitudinal edge of the table.

15 Claims, 1 Drawing Sheet

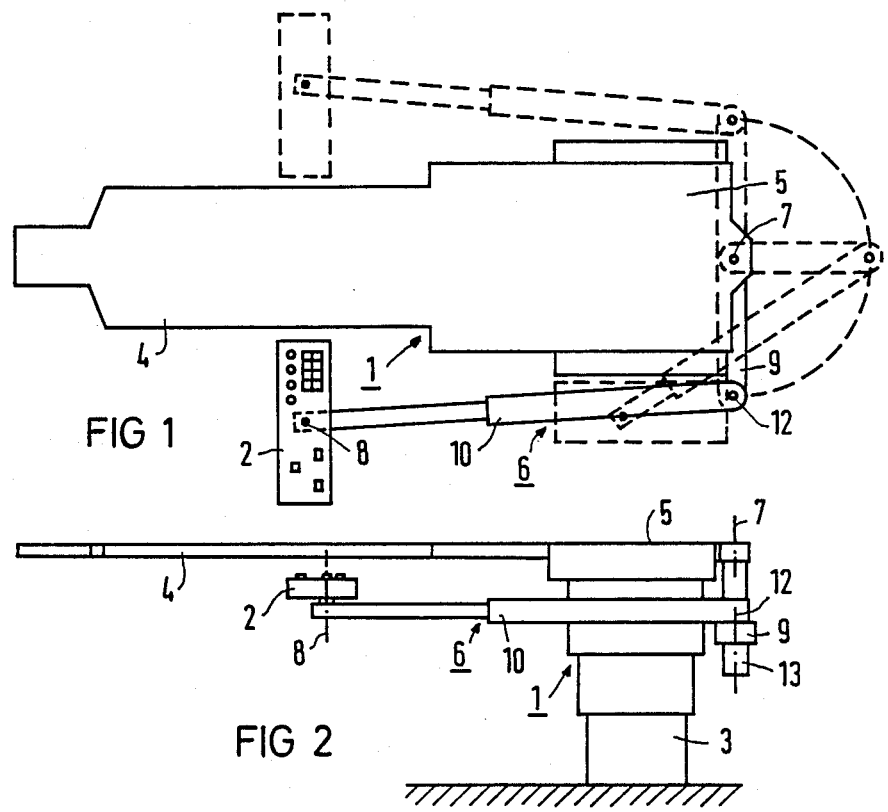
FIG 1
FIG 2
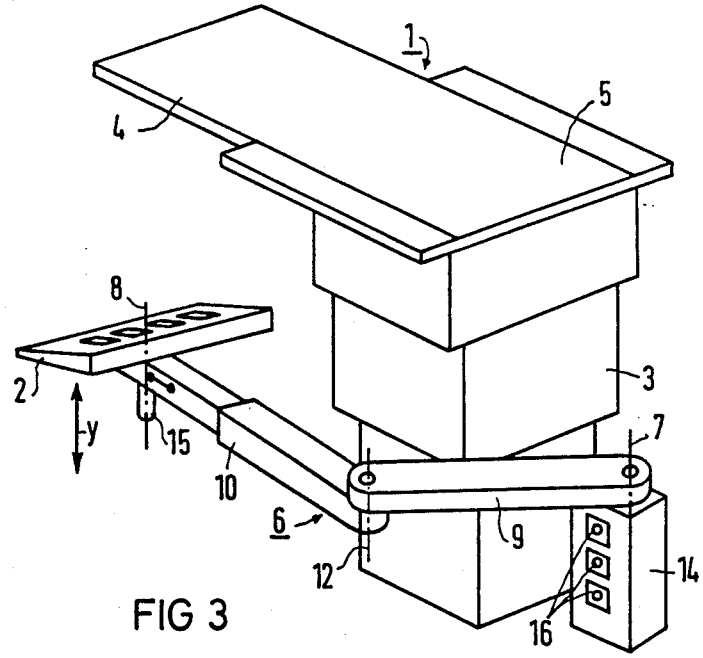
FIG 3

4,856,741

ADJUSTABLE PATIENT SUPPORT TABLE FOR AN X-RAY DIAGNOSTICS INSTALLATION

BACKGROUND OF THE INVENTION

1. Field of the Invention

The present invention is directed to an x-ray diagnostics installation having an adjustable patient support table, and in particular to such an installation wherein a control box for positioning the table is provided, the control box being adjustable in position relative to the table.

2. Description of the Prior Art

An x-ray diagnostics installation having an adjustable patient support table with a position-adjustable control box is disclosed in French Pat. No. 22 55 038. In this known apparatus, the control box is disposed beneath the support plate of the patient support table, and is pivotable around a horizontal axis. The control box can be moved from a standby position, wherein the control actuators on the control box are covered by the support plate, to a working position wherein the control actuators are freely accessible. Accessibility by an attendant or technician to a patient on the patient support table is thus possible without being impeded by the control box only if access to the control box is not needed, so that the control box can be pivoted beneath the support plate. If, however, access to the control box must be made in order to adjust the position of the patient, by adjusting the position of the support table, the attendant must make a choice as to whether the control box should be continuously accessible, and thus continuously impeding access to the patient, or whether the control box should be pivoted from beneath the support plate only when actuation of a control actuator is necessary, which is quite time-consuming. If access to the patient is needed outside of the region of the control box, for example, in the region of the head and of the patient support table, the control box can be pivoted from beneath the support table without impeding the attendant, but is then situated beyond the reach of the attendant, so that the attendant must physically move to the control box each time actuation of a control actuator is desired This makes work for the attendant in such a conventional installation uncomfortable and time-wasting.

SUMMARY OF THE INVENTION

It is an object of the present invention to provide an x-ray diagnostics installation having an adjustable patient support table, and a control box for the patient support table which is adjustable relative to the patient support table, wherein the control box can be disposed within the reach of an attendant at any time without impeding access of the attendant to a patient disposed on the support table.

This object is achieved in accordance with the principles of the present invention in an x-ray diagnostics installation wherein the control box is attached to a bracket which is mounted in the region of the foot end of the patient support table, and the control box is displaceable by means of the bracket in a direction parallel to a longitudinal edge of the patient support table. Regardless of the position of the patient support table from which the attendant wishes to have access to a patient on the table, the attendant can always bring the control box into a comfortable position within reach of the attendant, without the control box impeding access to the patent. The bracket on which the control box is supported does not impede accessibility to the patient because the bracket is secured in the region of the foot end of the patient support table. The bracket can be attached to a column mounted to the ceiling or to the floor of the room in which the installation is contained, or may be attached to the patient support table itself. If the x-ray source and the radiation receiver associated therewith are mounted, as is known, on a C-shaped frame partially surrounding the patient support table, access to adjustment of the C-shaped frame is also guaranteed by mounting the bracket or the column carrying the bracket, on which the control box is mounted in the region of the foot end of the patient support table.

An attendant can bring the control box to a comfortable position in an especially easy manner in an embodiment of the invention wherein the bracket is pivotably seated for movement around a vertical axis in the region of the foot end of the patient support table. The bracket may be pivotable around the vertical axis at the same time as being displaced along one of the longitudinal edges of the patient support table, so that the control box can always be disposed within easy reach of the attendant, regardless of the side of the patient support table at which the attendant is situated. If the control box is pivotably attached to the bracket, the bracket may be extensible in a telescoping fashion to permit height adjustment of the control box relative to a support plate of the patient support table.

The support plate to which the bracket is connected may itself be height-adjustable, which ensures that the control box always retains a height relative to the support plate which is comfortable for the attendant, even when the height of the support plate is adjusted.

Further freedom in the positioning of the control box is achieved in an embodiment wherein the bracket consists of first and second bracket sections connected to each other and pivotable around a vertical articulated axle. The first bracket section has a free end which is pivotable around the aforementioned vertical axis, and the second bracket section has a free end to which the control box is attached. If the overall bracket is to be extensible by telescoping, the second bracket section is preferably the telescoping section.

The first bracket section may have a length which is greater than or equal to one half of the width of the support plate, and the free end of the first bracket section may be pivotable from a point on the longitudinal axis of the patient support table by 90° toward both sides of the table. The second bracket section may be pivotable by more than 90° toward both sides of the table, proceeding from an initial position parallel to the first bracket section. It is then possible to bring the control box from one side of the patient support table to the other using a single bracket, so that the control box can be equally adjustable on both sides of the patient support table.

In a further embodiment of the invention, the control box can be moved to a standby position at the foot end of the patient support table during placement of the patient on the support plate of the table.

DESCRIPTION OF THE DRAWINGS

FIG. 1 is a plane view of a patient support table and position adjustable control box constructed in accordance with the principles of the present invention.

FIG. 2 is a side view of the apparatus shown in FIG. 1.

FIG. 3 is a perspective view of a further embodiment of a patient support, table with a position adjustable control box constructed in accordance with the principles of the present invention.

DESCRIPTION OF THE PREFERRED EMBODIMENTS

A patient support system constructed in accordance with the principles of the present invention, for use in a medical diagnostics installation, such as an x-ray diagnostics installation, is shown in the drawings. The system includes a patient support table 1 and a control box 2 . The patient support table is displaceable relative to the remainder of the x-ray diagnostics installation, and the control box 2 is displaceable relative to the patient support table 1. The patient support table 1 has a support plate 4 which is height-adjustable by means of a telescoping pedestal 3. The control box 2 is attached to a bracket 6 mounted in the region of the foot end 5 of the patient support table 1. The control box 2 can be displaced parallel to a longitudinal edge of the support plate 4 by means of the bracket 6. The bracket 6 is pivotable around a vertical axis 7 in the region of the foot end 5 of the patient support table 1. The control box 2 is attached to the bracket 6 so as to be pivotable around an axis 8. The bracket 6 consist of a first bracket section 9 and a second bracket section 10 which are connected to each other at a vertical articulated axle 12. The first bracket section 9 has a free end attached to and pivotable around the vertical axis 7, whereas the control box 2 is mounted to the free end of the second bracket 10. The second bracket section 10 may be a telescoping section.

Thus the control box 2 of the patient support system shown in the drawings can be positioned by an attendant so as to be within easy reach of the attendant, regardless of the position of the attendant with respect to the patient support table 1, and moreover, such positioning can be accomplished such that neither the control box 2 nor the bracket 6 impedes the attendant, or impedes access to the patient on the patient support table 1. As can be seen in FIG. 2, the bracket 6 (i.e., the first bracket section 9 thereof) is secured to the support plate 4 so that the control box 2 follows the movement of the support plate 4 when the support plate 4 is adjusted in height. The control box 2 will thus always be situated within reach of the attendant regardless of the height of the support plate 4, which may be adjusted. Moreover, the bracket 6, and thus the control box 2, may be individually height-adjustable relative to the support plate 4 by the operation of a motor 13 in a manner not shown in greater detail such as, for example, by means of a screw gear linkage.

As can also be seen in FIGS. 1 and 2, the first bracket section 9 has a length which is slightly greater than one half of the width of the support plate 4. If the free end of the first bracket section 9 is attached to the vertical axis 7 as shown in FIG. 1, which is coincident with a head-to-foot longitudinal axis of the support table 1, the first bracket section 9 can move from the position shown by dashed lines, parallel to the longitudinal axis, through 90° toward both sides of the support table 1. As can also be seen in FIGS. 1 and 2, the second bracket section 10 can be pivoted by more than 90° toward both sides of the table 1 proceeding from a position wherein the second bracket section 10 is parallel to the first bracket section 9. It is thus possible to pivot the control box 2 from one side of the patient support table 1 to the other side thereof, as indicated by the dashed lines in FIG. 1. Regardless of the side of the patient support table 1 at which the attendant is situated, the control box 2 can be positioned to be within easy reach of that attendant.

As also shown by dashed lines in FIG. 1, the control box 2 can be moved to a standby position disposed a the foot end 5 of the patient support table from either side of the patient support table 1. When the control box 2 is in this position, it does not impede access to a patient as the patient is placed on the support table 1.

A further embodiment of a patient support system constructed in accordance with the principles of the present invention for use in an x-ray diagnostics installation is shown in FIG. 3, wherein components identical to those shown in FIGS. 1 and 2 have been provided with the same reference numbers. The embodiment of FIG. 3 differs from the embodiment of FIGS. 1 and 2 in that the bracket 6 carrying the control box 2 in the embodiment of FIG. 3 is mounted on a column 14, pivotable around the aforementioned vertical axis 7. The column 14 is attached to the floor of the room in which the apparatus is installed in the region of the foot end 5 of the patient support table 1. The bracket 6 again consists of a first bracket section 9 and a second bracket section 10, which is extensible in a telescoping fashion. The control box 2 is attached to the second bracket section 10 in a height-adjustable manner in the direction of the double arrow y by means of a schematically illustrated guide 15, so that the height of the control box 2 can be adapted to the stature of the attendant, or to the height of the support plate 4. The column 14 may be provided with a plurality of connections 16 for auxiliary apparatus. Although modifications and changes may be suggested by those skilled in the art it is the intention of the inventor to embody within the patent warranted hereon all changes and modifications as reasonably and properly come within the scope of his contribution to the art.

I claim as my invention:

1. A patient support system for use in an x-ray diagnostics installation having a plurality of components, said system comprising:

a control box having controls thereon for controlling at least said patient support system;

a patient support table having a head end and a foot end defining a longitudinal axis therebetween, said patient support table having longitudinal edges parallel to said longitudinal axis; and bracket means for permitting movement of said control box to a standby position at said foot end of said patient support table, said control box in said stand by position lying adjacent said foot end of said patient support table generally parallel to said longitudinal axis to permit access to said patient support table;

said bracket means having a first end attached at said foot end of said patient support table and a second end attached to said control box for permitting displacement of said control box parallel to a longitudinal edge of said patient support table.

2. A patient support system as claimed in claim 1, wherein said first end of said bracket means is mounted to said foot end of said support table for pivoting around a vertical axis.

3. A patient support system as claimed in claim 1, wherein said control box is pivotably attached at said second end of said bracket.

4. A patient support system as claimed in claim 1, wherein said bracket means is extensible by telescoping.

5. A patient support system as claimed in claim 1, wherein said patient support table has a support plate, and further comprising means for adjusting the height of said control box relative to said support plate.

6. A patient support system as claimed in claim 1, wherein said patient support table has a support plate, and wherein said bracket means is connected to said support plate.

7. A patient support system as claimed in claim 6, further comprising means for adjusting the height of said support plate.

8. A patient support system as claimed in claim 1, wherein said bracket means comprises:
- a first bracket section having a free end functioning as said first end of said bracket means and attached to said patient support table at said foot end thereof, and having an opposite end;
- a second bracket section having a free end functioning as said second end of said bracket means and attached to said control box, and having an opposite end; and
- means for connecting said opposite ends of said first and second bracket sections permitting pivoting around a vertical articulated axle.

9. A patient support system as claimed in claim 8, wherein said second bracket section is extensible by telescoping.

10. A patient support system for use in an x-ray diagnostics installation having a plurality of components, said system comprising:
- a control box having controls therein for controlling at least said patient support system;
- a patient support table having a head end and foot end defining a longitudinal axis therebetween, said patient support table having longitudinal edges parallel to said longitudinal axis;
- bracket means having a first end attached at said foot end of said patient support table at a second end attached to said control box for permitting displacement of said control box parallel to a longitudinal edge of said patient support table, said bracket means including:
  - a first bracket section having a free end functioning as said first end of said bracket means and attached to said patient support table at said foot end thereof, and having an opposite end;
  - a second bracket section having a free end functioning as said second end of said bracket means and attached to said control box, and having an opposite end;
  - means for connecting said opposite ends of said first and second bracket sections permitting pivoting around a vertical articulated axle;

wherein said first bracket section has a length which is greater than or equal to one-half of the width of said patient support table, and further comprising means for pivotably attaching said free end of said first bracket section to said patient support table at a point on said longitudinal axis and permitting pivoting from a position parallel to said longitudinal axis through 90° toward both side of said patient support table or a vertical axis through said point, and wherein said means for connecting said first and second bracket sections permits pivoting of said second bracket section from a position parallel to said first bracket sections through 90° towards both sides of said patient support table.

11. A patient support system for use in a medical diagnostics installation having a plurality of components, said system comprising:
- a patient support table adjustable in position relative to said components of said installation having a head end and a foot end defining a longitudinal axis therebetween;
- a first bracket section having a first end mounted for pivoting about a vertical axis extending through said longitudinal axis at said foot end of said patient support table, and having a second end;
- a second bracket section having a first end attached to said second end of said first bracket section for pivoting around a further vertical axis, and having a second end; and
- a control box having controls thereon permitting an attendant to adjust the position of said patient support table, said control box attached to said second end of said second bracket section, and said first and second bracket sections in combination permitting displacement of said control box along a longitudinal edge of said patient support table.

12. A patient support system as claimed in claim 11, wherein said second bracket section is extensible by telescoping.

13. A patient support system as claimed in claim 11, wherein said first bracket section has a length which is greater than or equal to one half of the width of said patient support table.

14. A patient support system as claimed in claim 11, wherein said first bracket section is pivotable through 90° from a position parallel to said longitudinal axis toward either side of said patient support table.

15. A patient support system as claimed in claim 11, wherein said second bracket section is pivotable through 90° from a position parallel to said first bracket section.

* * * * *